United States Patent [19]

Hetherington

[11] Plant 4,701

[45] Apr. 28, 1981

[54] ORCHID-SLC. PRECIOUS STONES-TRUE BEAUTY

[75] Inventor: Ernest E. Hetherington, Arcadia, Calif.

[73] Assignee: Fred A. Stewart Inc., San Gabriel, Calif.

[21] Appl. No.: 140,658

[22] Filed: Apr. 15, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Edmond F. Shanahan

[57] ABSTRACT

A new and distinct variety of orchid, and more particularly, a *Sophrolaeliocattleya* hybrid (herein abreviated Slc.) having dwarf growth habit and flowers of a red color.

The new variety is distinctive from its parents, and from plants of the same hybrid population, and from other red flowered orchids, by the compact growth habit, free-blooming habit, and clear red color.

2 Drawing Figures

DISCOVERY OF THE NEW VARIETY

The orchid of this application was discovered by the undersigned discoverer as an outstanding member of a large population of Slc. Precious Stones. Slc. Precious Stones had been developed in the orchid nursery of Fred A. Stewart Inc., at San Gabriel, Calif., by crossing Sophrolaelia Psyche 'Garnet' by Cattleya aclandiae 'Paul Lee'. The Slc. Precious Stones hybrid was registered by the Stewart Nursery with the Royal Horticultural Society, London, England, on Oct. 23, 1971, being designated in the registration as "Stewart cross #1250, Slc. Precious Stones."

The original plant of the new variety first appeared in the year 1972, and was immediately recognized as superior in growth, blooming, and flower color.

After its discovery, the original plant was placed in the laboratories of the Fred A. Stewart Inc. nursery, and during subsequent years, a large number of substantially identical plants were asexually reproduced by the meristem method. All of these plants reproduced true to the original plant in both plant and flower, and in other characteristics; all continued to be readily distinguishable from both parents and the other plants of the same hybrid population. The flowers were recognizably superior in color and physical structure; the plant as a whole has a dwarf, compact growth habit which distinguishes it from its relatives.

A large inventory of the plants has now been produced by the meristem culture method. The new variety has been named Slc. Precious Stones-True Beauty; and the population of the new variety is carried under the code number SM-276.

DESCRIPTION OF THE PLANT

The plant and its flowers are illustrated in the two accompanying color photographs.

The leaves are coriacious, 7 cm. to 8 cm. long, and irregularly marked with small purple spots (British Horticultural Colour Chart Indian Lake, 170-826), a typical characteristic of the *C. aclandiae* parent. The leaf is a typical bifoliate-cattleya leaf.

The growth is strong, compact, and erect. The plant's rhizome is short. Dormant vegetative bulbs tend to sprout readily, resulting in several bulbs in a pot, a characteristic which is uncommon in cattleyas, particularly red cattleyas. Plant growth habit is 12 cm. to 16 cm. on maturity, which is miniature for a cattleya. Plants of the new variety have been virus and pathogen free throughout the seven years of development.

DESCRIPTION OF THE FLOWER

The flower has an unusual red color (see the accompanying color photos) which has been uncommon among cattleya orchids.

Red is one of the most sought after colors in Cattleya hybridizing, and one of the most difficult to obtain.

The task is doubly difficult where miniature growth habit, better flower shape and substance are desired along with the red coloration of the petals. Most red Cattleyas are poor of shape, tending to be rather open, and poor of color; and also tending to have more of a purple or plum color than a true red color.

The flowers of the new variety have petals which are flat, well carried without twisting, turning or recurving. The three sepals are in symmetrical balance to the petals and create a good round shape to the flower as a whole. Both sepals and petals are uniform blood-red most of the flower life. (The color is B.H.C.C. Page 166, Blood Red, #210, Intensity #820/1 to 820/3, Ref. Blood Red.)

The Indian Lake color labellum (B.H.C.C. Page 170 Indian Lake, Intensity #826/2 to #826/3, Ref. Nicotiana × sanderae) is squarish and marked with a small patch of barium yellow (B.H.C.C. Page 131, Barium Yellow, Intensity #503/2, Ref. None). The column is lemon yellow (B.H.C.C. Page 4 Lemon Yellow, Intensity #4/3, Ref. None), heavily flushed with fuchsia purple (B.H.C.C. Page 28, Fuchsia, #199, Intensity #28 to #28/2, Ref. *Lathyrus sylvestris*). The side lobes of the labellum are the same fuchsia-purple color, and are carried erectly over the column.

The new cultivar Slc. Precious Stones-True Beauty can carry up to five flowers, approximately 6 cm. in diameter, on a mature well grown plant. Two to four flowers is average for most Cattleyas. The flowers are well carried on an erect stem. The substance of the flowers is exceptionally heavy. The flowers last several weeks. The red color holds for most of the flower life, but changes to a brick-red color on maturity. See B.H.C.C. 106/016. The blooming season is variable, with winter/spring predominating. Twice a year bloom is quite common.

I claim:

1. A new and distinct variety of orchid, of the genus Sophrolaeliocattleya, discovered as an individual plant outstanding for its red colored flowers and compact growth habit among a large population of the particular hybrid group known as Slc. Precious Stones.

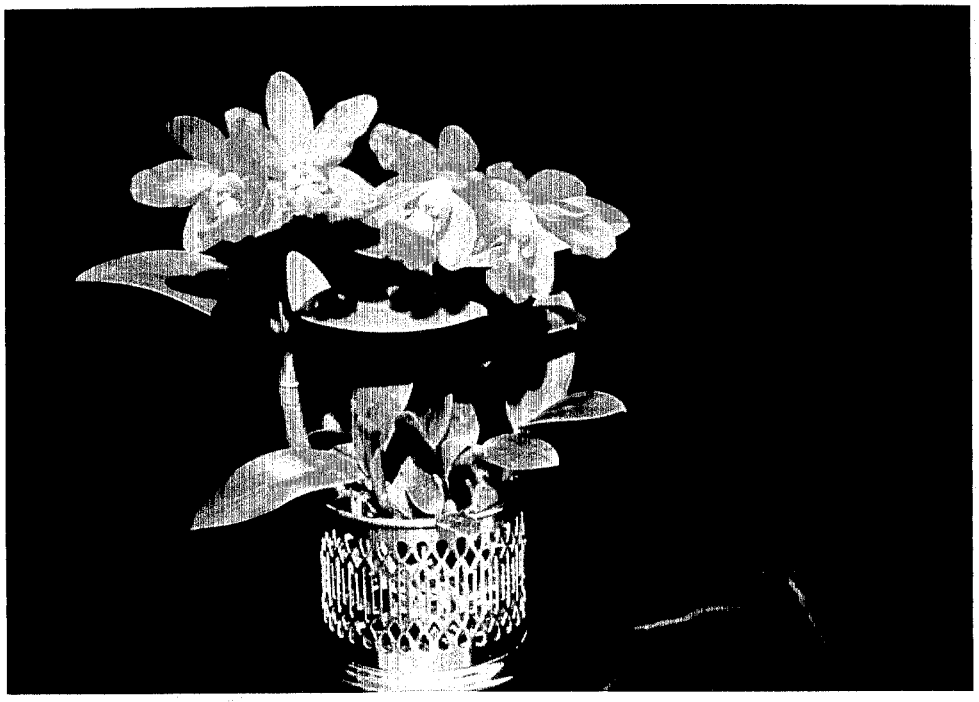
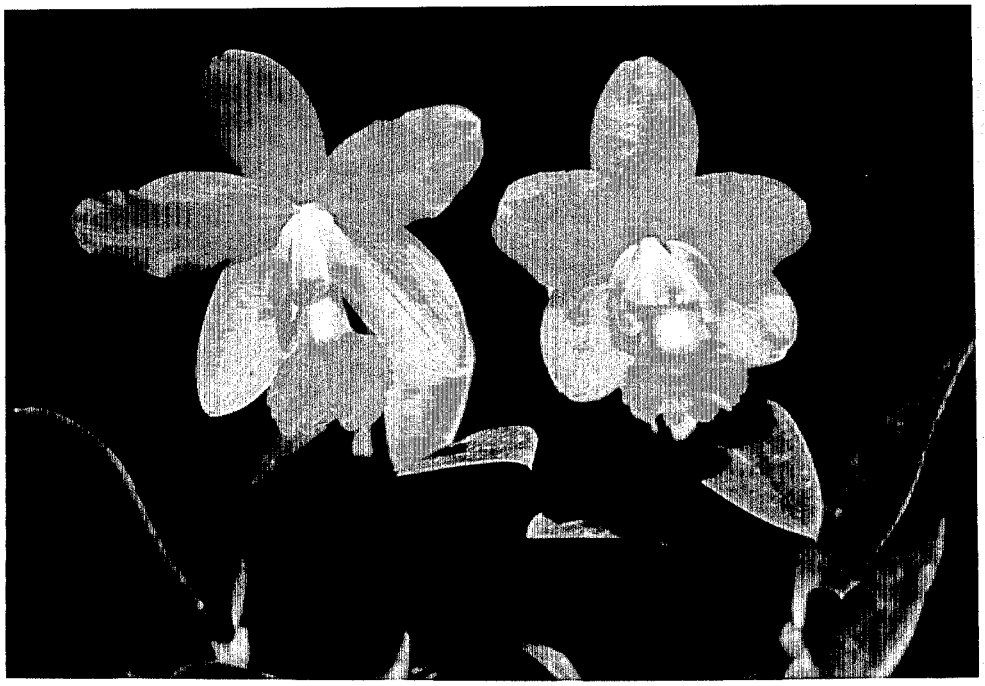

* * * * *